United States Patent

Minato et al.

[11] 4,400,525
[45] Aug. 23, 1983

[54] POLYGLYCIDYL COMPOUNDS

[75] Inventors: Ichiro Minato, Kobe; Koichi Shibata, Ashiya; Kimiya Fujinami, Takarazuka, all of Japan

[73] Assignee: Takeda Chemical Industries, Ltd., Osaka

[21] Appl. No.: 322,205

[22] Filed: Nov. 17, 1981

[30] Foreign Application Priority Data

Nov. 28, 1980 [JP] Japan .................... 55-168373

[51] Int. Cl.$^3$ ........................................ C07D 303/36
[52] U.S. Cl. .................... 549/552; 528/341; 528/407
[58] Field of Search .................. 260/348.44; 549/514, 549/552

[56] References Cited

U.S. PATENT DOCUMENTS 3,312,664  4/1967  Bremmer ................. 260/348.44
3,683,044  8/1972  Huang et al. ............ 260/348.44
3,843,565  10/1974  Yamamoto et al. ....... 260/348.44

OTHER PUBLICATIONS

F. L. Weitl et al., Jour. Am. Chem. Soc., vol. 101, No. 10, May 9, 1979, pp. 2728-2731.

Primary Examiner—Norma S. Milestone
Attorney, Agent, or Firm—Antonelli, Terry & Wands

[57] ABSTRACT

Disclosed is a novel polyglycidyl compound useful as polyfunctional epoxy resins excellent in adhesion, heat resistance and strength. This novel polyglycidyl compound has the general formula:

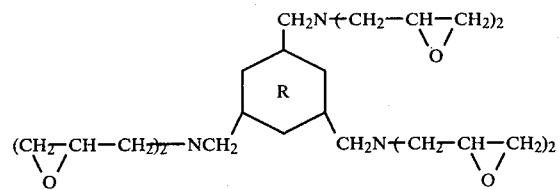

(wherein

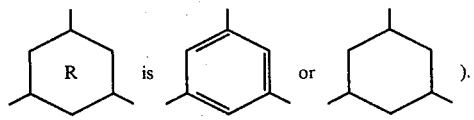

A method for producing this polyglycidyl compound is also disclosed.

3 Claims, 2 Drawing Figures

POLYGLYCIDYL COMPOUNDS

The present invention relates to novel polyglycidyl compounds and a method for producing same. More particularly, it relates to polyglycidyl compounds useful especially as polyfunctional epoxy resins and a method for producing same.

Recently, use of polyfunctional epoxy resins as matrix resins for composite materials such as carbon fiber reinforced composite materials has attracted attention and development of the epoxy resins more excellent in adhesion, heat resistance and strength has been demanded.

The inventors have made intensive researches on various derivatives of 1,3,5-tris(aminomethyl)benzene (sometimes referred to as "MTA" hereinafter) and 1,3,5-tris(aminomethyl)cyclohexane (sometimes referred to as "H$_6$MTA" hereinafter). As a result, it has been found that polyglycidyl derivatives of these triamines have excellent properties as polyfunctional epoxy resins.

That is, the present invention relates to polyglycidyl compounds represented by the general formula [I]:

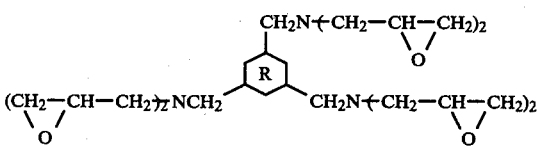

(wherein

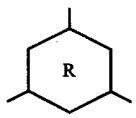

represents

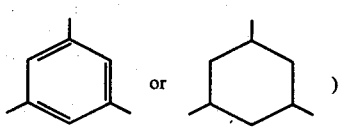

and a method for producing polyglycidyl compounds represented by the general formula [I]:

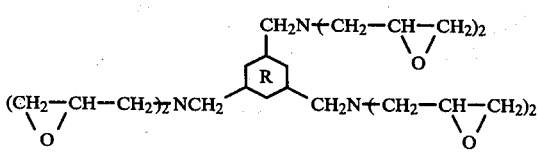

(wherein

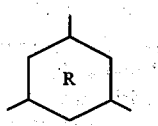

represents

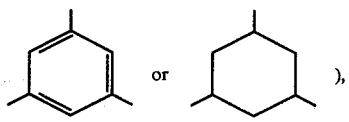

which comprises reacting an epihalohydrin with a triamine represented by the general formula:

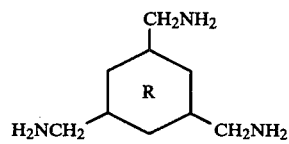

(wherein

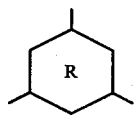

has the same meanings as defined above) and then treating the reaction product with an alkali.

Figure 1:
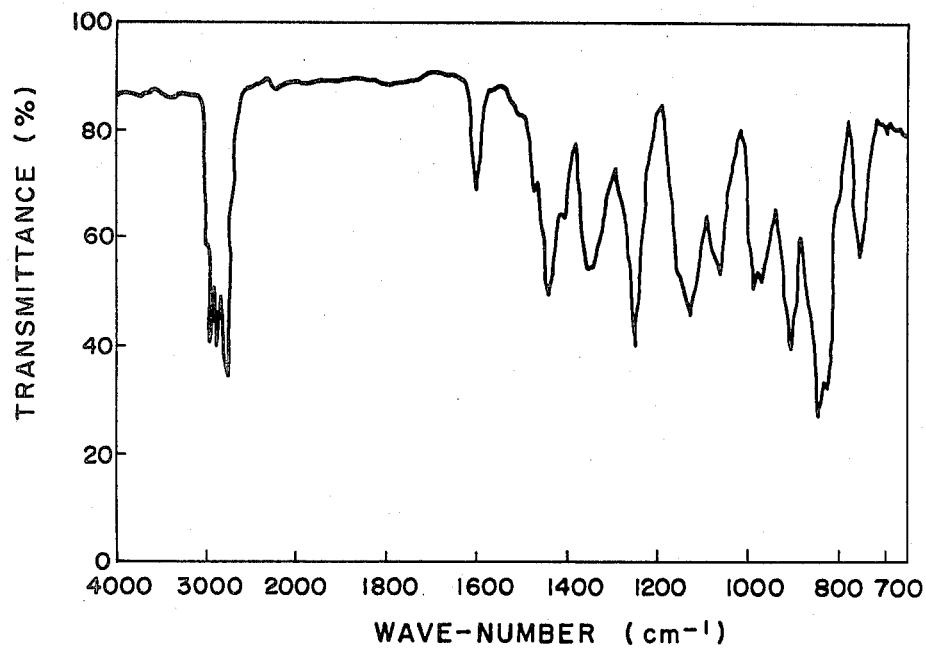
Figure 2:
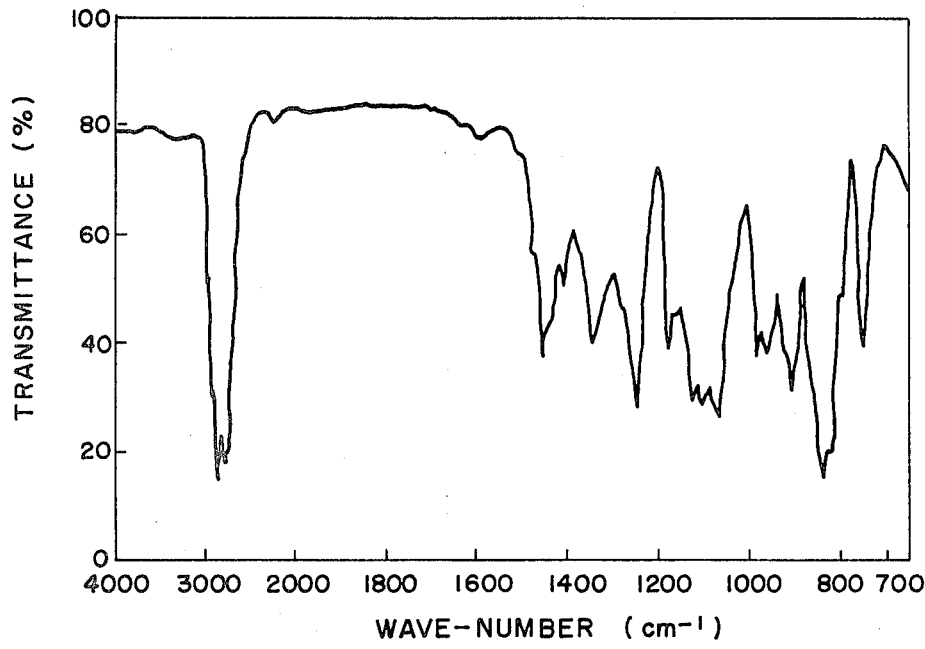

In the accompanying drawings, FIG. 1 and FIG. 2 show infrared absorbing spectrum of the product obtained in Example 1 and Example 2, respectively.

The compound [I] of the present invention can be produced by reacting 1,3,5-tris(aminomethyl) benzene (MTA) or 1,3,5-tris(aminomethyl) cyclohexane (H$_6$MTA) with an epihalohydrin, especially, epichlorohydrin and thereafter subjecting the reaction product to dehydrohalogenation treatment in the presence of an alkali. The starting materials MTA and H$_6$MTA may be produced by the methods as disclosed in Japanese patent applications No. 67169/79 and No. 67170/79. That is, MTA can be produced by reducing, under the presence of a catalyst such as Raney nickel, a starting material of 1,3,5-tricyanobenzene obtained by ammoxydation of mesitylene. H$_6$MTA can be produced by further reducing aromatic ring of the MTA under the presence of a reducing catalyst. H$_6$MTA can also be obtained directly from 1,3,5-tricyanobenzene by reducing cyano groups and aromatic ring thereof.

Thus obtained MTA or H$_6$MTA is first reacted with an epihalohydrin. This addition reaction may be carried out in accordance with known methods. For instance, the epihalohydrin is used preferably in an excess amount with respect to MTA or H$_6$MTA, which is ordinarily 6 to 20 moles per 1 mole of these triamines. Reaction temperature is preferably within the range of about 20° to 60° C. These starting materials may be reacted without solvents, but the reaction may also be carried out in solvents such as organic solvents, water and the like to prevent abrupt exothermic reaction. Such addition reaction of the first stage will generally be completed within 2 to 5 hours although it depends on reaction conditions. Then, an alkali is allowed to act on thus obtained epihalohydrin addition products to carry out dehydrohalogenation reaction thereby to bring about ring closure to form epoxy groups. Alkali metal hydroxides such as sodium hydroxide, potassium hydroxide or aqueous solutions thereof may be suitably used as alkalis for the ring closure reaction. Generally, the alkalis are used in an excess amount. After completion of the reaction, excess epihalohydrin and, if necessary, solvents are distilled out under reduced pressure. To the obtained reaction product is added an organic solvent such as benzene, toluene or xylene. Insoluble matter is filtered off and filtrate is washed several times with water or an aqueous sodium chloride solution. Then, the organic solvent is distilled out to obtain an objective product.

The polyglycidyl compounds of the present invention represented by the general formula [I] are especially useful as epoxy resins which provide hardened products having excellent characteristics. For example, the compounds of the present invention are liquid so that they are convenient for working. Moreover, they can be hardened with known hardening agents. Examples of such hardening agents are aliphatic or aromatic acid anhydrides such as maleic anhydride, succinic anhydride, tetrahydrophthalic anhydride, hexahydrophthalic anhydride, 3,6-endomethylenetetrahydrophthalic anhydride, dodecenylsuccinic anhydride, phthalic anhydride, etc., aliphatic or aromatic polyamines such as monoethylamine, n-propylamine, isopropylamine, n-butylamine, hexylamine, benzylamine, ethylenediamine, aniline, 4,4'-diaminodiphenylmethane, 4,4'-diaminodiphenylether, 4,4'-diaminodiphenyl sulfone, etc., aniline resin, polyamide resin, imidazoles, mercaptans, $BF_3$ compounds, etc. Furthermore, the polyglycidyl compounds of the present invention have self-hardening property and can be characteristically hardened without hardening agents.

The hardened products thus obtained have excellent adhesive property and heat resistance and high strength. When the compounds of the present invention are used as epoxy resins, there may be optionally added thereto compounding agents such as extenders, reinforcing agents, fillers, pigments, etc. Furthermore, if necessary, other known epoxy resins may be blended with the present compounds.

When the polyglycidyl compounds of the present invention are used as epoxy resins, the compounds, have excellent characteristics as mentioned above and so can be used as surface treating agents for various fibers such as carbon fiber and as matrix resins of various fiber reinforced resins, and moreover, as crosslinking agents or modifiers for acrylic resins and polyester resins. Furthermore, they are useful as stabilizers for unsaturated polyester resins.

Furthermore, the polyglycidyl compounds of the present invention are excellent in adhesive property and can be bonded to polypropylene films under specific conditions to which the commercially available epoxy resins cannot be bonded.

REFERENCE EXAMPLE 1

Preparation of 1,3,5-tricyanobenzene 18.2 parts of vanadium pentoxide was added to 150 parts of a 33% aqueous solution of oxalic acid and the mixture was heated to about 100° C. on a water bath to dissolve vanadium pentoxide. The solution was referred to as solution A. A solution obtained by dissolving 20 parts of chromium oxide (VI) in 150 parts of a 33% aqueous solution of oxalic acid as mentioned above was referred to as solution B. Solutions A and B were homogeneously mixed.

To this mixed solution was added 300 parts of anatase type titanium oxide powder burned at 800° C. and water was evaporated therefrom while they were mixed. Thus obtained wet slurry was molded by an extruder into a cylindrical shape having a diameter of 4 mm and a length of 5 mm. Thus obtained molded products were dried at 100° C. for 15 hours and thereafter burned at 500° C. for 4 hours in air to obtain a catalyst.

About 200 ml of thus obtained catalyst was packed in an ordinary fixed bed reactor and a mixed gas consisting of 0.5 mole % of mesitylene, 7 mole % of ammonia and 92.5 mole % of air was reacted under normal pressure at a space velocity of 1000 hr$^{-1}$ (at normal temperature and pressure) while maintaining the temperature of medium in bath at 360° C. to obtain 1,3,5-tricyanobenzene (MTN) in a yield of 51.2 mole %.

REFERENCE EXAMPLE 2

Preparation of 1,3,5-tris(aminomethyl) benzene 15 g of 1,3,5-tricyanobenzene (MTN) was charged into a magnetically stirring type autoclave having a 300 ml capacity together with 15 g of Raney nickel-chromium catalyst (atomic ratio: Ni:Cr=49:1), 27 ml of methanol, 63 ml of m-xylene and 0.18 g of sodium hydroxide. Hydrogen was injected thereinto under an initial pressure of 100 kg/cm$^2$G and reaction was effected at 100° C. to cause absorption of 0.59 mole of hydrogen for 35 minutes. The catalyst was filtered off and the solvent was distilled out. Then, distillation under reduced pressure was effected to obtain 12.8 g of colorless crystal of 1,3,5-tris(aminomethyl) benzene (MTA). The product had a melting point of 49° to 51° C. and a boiling point of 136° to 139° C./0.4 mmHg.

REFERENCE EXAMPLE 3

Preparation of 1,3,5-tris(aminomethyl) cyclohexane.

30 g of 1,3,5-tris(aminomethyl) benzene (MTA) obtained in Reference Example 2 together with 3 g of 5% ruthenium-alumina catalyst (manufactured by Japan Engelhard Co., Ltd.), 60 g of water and 0.75 g of sodium hydroxide were charged in a magnetically stirring type autoclave having a 300 ml capacity. High pressure hydrogen was injected thereinto under an initial pressure of 120 kg/cm$^2$G and reaction was effected at 115° C. for 25 minutes to cause absorption of 0.61 mole of hydrogen.

The catalyst was filtered off and the solvent was distilled out. Thereafter, distillation under reduced pressure was carried out to obtain 26.8 g of 1,3,5-tris(aminomethyl) cyclohexane (H$_6$MTA). This H$_6$MTA was a colorless and transparent liquid of low viscosity which had a boiling point of 127° to 128° C./1 mmHg.

REFERENCE EXAMPLE 4

Preparation of 1,3,5-tris(aminomethyl)cyclohexane

In a magnetically stirring type autoclave having a 300 ml capacity were charged 20 g of 1,3,5-tricyanobenzene obtained in Reference Example 1 together with 80 ml of 25% aqueous ammonia, 300 mg of sodium hydroxide and 4 g of commercially available 5% rhodium-alumina catalyst and reaction was effected at 105° C. for 70 minutes under high pressure hydrogen having an initial pressure of 120 kg/cm$^2$ to result in absorption of 0.95 mole of hydrogen to obtain H$_6$MTA in which both the nitriles and the nucleus were reduced, in a yield of 45%.

EXAMPLE 1

In a 2 l four-necked flask provided with a stirrer, a hot dropping funnel and a thermometer were charged 616 g of epichlorohydrin and 32.7 g of water and they were warmed to 35° C. with stirring. To this solution was dropped 100 g of 1,3,5-tris(aminomethyl)benzene molten at 53° C. over a period of about 1.5 hour. Since violent heat generation occurs simultaneously with initiation of dropping of 1,3,5-tris(aminomethyl)benzene, the flask was cooled and reaction temperature was kept at 35° to 40° C. Reaction was effected for further 3 hours at the same temperature and thereafter 320 g of 50% aqueous NaOH solution was dropped thereto over a period of about 25 minutes keeping the temperature at 35° to 40° C.

Then, excess epichlorohydrin and water were removed at 40° C. over a period of 5 hours under a reduced pressure of 10 mmHg to 2 mmHg using a rotary evaporator to obtain a mixture of an oily material and a white crystal. To the mixture was added 600 ml of toluene cooled with ice and then the mixture was filtered. The filtrate was once washed with 100 ml of 3% aqueous NaCl solution and then washed again with 50 ml of water. Toluene was distilled out under a reduced pressure of 10 mmHg to obtain 245 g of slightly yellow transparent liquid which had a viscosity of 11,350 centipoises (25° C.) and an epoxy equivalent of 93.1 (theoretical value 83.6).

|  | Elementary analysis | | |
|---|---|---|---|
|  | C % | H % | N % |
| Calcd: | 64.65 | 7.84 | 8.38 |
| Found: | 64.36 | 7.81 | 8.11 |

IR absorption spectrum of the product is shown in FIG. 1. Measurement of NMR spectrum (CDCl3) of the product showed that a signal of singlet due to proton of the aromatic ring appeared at 7.22 ppm and a signal of complicated multiplet due to the other protons appeared at 2.2 to 4.1 ppm and the intensity ratio was 1 to 12.1. From these analytical values and spectra it was confirmed that the product was N,N,N',N',N'',N''-hexaglycidyl-1,3,5-tris (aminomethyl)benzene.

EXAMPLE 2

Reaction procedure of Example 1 was repeated except that 100 g of 1,3,5-tris(aminomethyl)cyclohexane was substituted for 1,3,5-tris(aminomethyl)benzene used in Example 1 and 593 g of epichlorohydrin, 32 g of water and 306 g of 50% aqueous solution of sodium hydroxide were used, whereby 227 g of a colorless and transparent liquid was obtained. The product had an epoxy equivalent of 95.5 (theoretical value 84.6) and a viscosity of 9,183 centipoises (25° C.)

|  | Elementary analysis | | |
|---|---|---|---|
|  | C % | H % | N % |
| Calcd: | 63.88 | 8.93 | 8.28 |
| Found: | 63.97 | 8.94 | 8.02 |

IR spectrum of the product is shown in FIG. 2. Furthermore, measurement of NMR spectrum (CDCl3) showed complicated multiplet spectrum at 0.2 to 4.1 ppm composed of the peculiar absorption pattern due to proton of skeleton of H6MTA which overlapped the signal due to proton of glycidyl. It was confirmed therefrom that the product was N,N,N',N',N'',N''-hexaglycidyl-1,3,5-tris(aminomethyl)cyclohexane.

EXPERIMENTAL EXAMPLES 1-13

The polyglycidyl compounds synthesized in Examples 1 and 2 and the known epoxy resins were hardened with diaminodiphenylmethane (DDM), methyl nadic anhydride (MNA) or a polyamide by using the conventional procedures. The mechanical and thermal properties of the cast sheet prepared were measured and adhesion test was also carried out. The results are shown in Tables. The hardening was carried out by stepwise elevation of temperature.

TABLE 1

| Experimental Examples | Epoxy resins | Hardening agent DDM | Hardening conditions*2 | Heat distortion temperature of cast sheet ASTM D-648 | Adhesion to polyester film*3 |
|---|---|---|---|---|---|
| 1 | Polyglycidyl compound obtained in Example 1 | 59.3 phr | A | more than 200° C. | ⊚ |
| 2 | Polyglycidyl compound obtained in Example 2 | 58.6 | A | more than 200° C. | ⊚ |
| 3 | Tetrafunctional epoxy resin*1 from meta-xylylene-diamine | 50 | A | 190° C. | O |
| 4 | Epikote 828 (epoxy value 188.7) | 26 | B | 155° C. | X | phr: parts per hundred parts of resin
*1PGA-X manufactured by Mitsubishi Gas Chemical Company Incorporated, N,N,N',N'—tetraglycidyl meta-xylylene-diamine
*2Hardening condition A: (80° C., 3 hr) + (150° C., 3 hr) + (180° C., 3 hr)
Hardening condition B: (80° C., 3 hr) + (150° C., 3 hr)
*3⊚Not separable at all.
O Separable with difficulty.
X Separable with ease.

TABLE 2

| Experimental Examples | Epoxy resins | Hardening agents Kind | Hardening agents Amount (phr) | Hardening condition*5 | Bending strength of cast sheet (JIS K-6911 which is a method based on ASTM D-790-71) Bending strength kgf/mm² | Bending strength of cast sheet (JIS K-6911 which is a method based on ASTM D-790-71) Modulus of elasticity kgf/mm² | Heat distortion temperature of cast sheet ASTM D-648 (°C.) |
|---|---|---|---|---|---|---|---|
| 5 | Polyglycidyl compound obtained in | DDM | 59.3 | C | 12.9 | 465 | 234 |

TABLE 2-continued

| Experimental Examples | Epoxy resins | Hardening agents Kind | Hardening agents Amount (phr) | Hardening condition*5 | Bending strength of cast sheet (JIS K-6911 which is a method based on ASTM D-790-71) Bending strength kgf/mm² | Bending strength of cast sheet (JIS K-6911 which is a method based on ASTM D-790-71) Modulus of elasticity kgf/mm² | Heat distortion temperature of cast sheet ASTM D-648 (°C.) |
|---|---|---|---|---|---|---|---|
| 6 | Example 1 Polyglycidyl compound obtained in Example 1 | " | 29.6 | " | 13.2 | 476 | 246 |
| 7 | Polyglycidyl compound obtained in Example 1 | MNA*4 | 171 | " | 11.0 | 429 | 234 |
| 8 | PGA-X | DDM | 49.1 | " | 12.7 | 398 | 190 |
| 9 | " | MNA | 158 | " | 10.4 | 342 | 186 |

*4Methyl nadic anhydride manufactured by Hitachi Chemical Co., Ltd.
*5Hardening condition C: (80° C., 5 hr) + (150° C., 2 hr) + (180° C., 2 hr)

TABLE 3

| Experimental Examples | Epoxy resins | Hardening agents Kind | Hardening agents Amount (phr) | Hardening conditions | Adhesion to polypropylene film*6 Surface*7 | Adhesion to polypropylene film*6 Back-side (kgf/25 mm)*8 |
|---|---|---|---|---|---|---|
| 10 | Epikote 828 | DDM | 26.4 | 100° C., 3 hr | ⊚ | X (0.1) |
| 11 | PGA-X | " | 49.1 | " | ⊚ | Δ (0.2) |
| 12 | Polyglycidyl compound obtained in Example 1 | " | 58.7 | " | ⊚ | ⊚ (at least 2.0) |
| 13 | Epikote 828 | G-740*9 | 43 | " | ⊚ | Δ (0.4) |

*6 180° peeling test in accordance with JIS K-6854 which is a method based on ASTM D-903-49 using RXC-5 having a thickness of 50μ manufactured by Tokyo Cellophane Paper Co., Ltd.
*7The surface was subjected to corona discharge treatment. '⊚' means that no separation occurred and breakage of material (film) occurred.
*8The back-side was subjected to no treatment.
⊚Not separable at all and breakage of material (film) occurred.
Δ Separable.
X Easily separable.
*9Goodmide G740 which is a polyamide manufactured by Toto Chemical Co., Ltd.

EXPERIMENTAL EXAMPLE 14

Two iron plates (100×25×1.6 mm) surfaces of which were subjected to abrasive treatment and washed with trichloroethylene were bonded under the pressure of 9 kgf/cm² using the polyglycidyl compound produced in Example 1 by self-hardening of the compound at 140° C. for 12 hours. Tensile adhesive shear strength thereof was 162 kgf/cm² (JIS-K6850 which is based on ASTM D-1002-64).

Similarly, two iron plates were bonded using the polyglycidyl compound produced in Example 2. Tensile adhesive shear strength of thus bonded iron plates was 165 kgf/cm² (JIS-K6850).

We claim:

1. A polyglycidyl compound which is represented by the general formula:

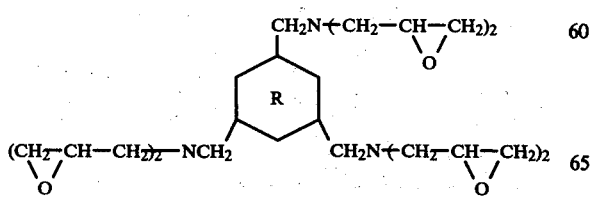

wherein represents

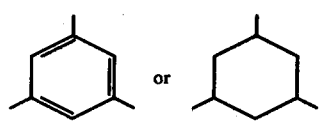

2. A polyglycidyl compound according to claim 1, wherein

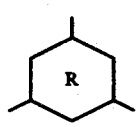

in the general formula is

3. A polyglycidyl compound according to claim 1, wherein
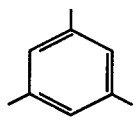
in the general formula is
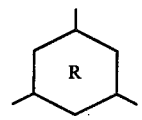
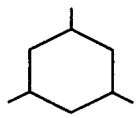
* * * * *